United States Patent
Rosengart et al.

(10) Patent No.: US 6,322,536 B1
(45) Date of Patent: *Nov. 27, 2001

(54) MINIMALLY INVASIVE GENE THERAPY DELIVERY AND METHOD

(75) Inventors: Todd K. Rosengart, Tenafly, NJ (US); Ronald G. Crystal, Potomac, MD (US)

(73) Assignee: Cornell Research Foundation, Inc., Ithaca, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/393,873

(22) Filed: Sep. 10, 1999

Related U.S. Application Data (63) Continuation-in-part of application No. 09/035,892, filed on Mar. 6, 1998, now Pat. No. 5,997,509.

(51) Int. Cl.[7] .................................................. A61M 5/178
(52) U.S. Cl. ............... 604/164.01; 604/19; 604/116; 604/272; 604/181; 604/187; 128/898; 600/372; 600/374; 606/8
(58) Field of Search ........................ 604/1, 95, 115–17, 604/181, 187–88, 164, 207–8, 211, 218, 246, 272, 19–22, 95.01, 95.04, 95.05; 606/8; 600/372–74; 128/898

(56) References Cited

U.S. PATENT DOCUMENTS

| | | |
|---|---|---|
| 510,413 | 12/1893 | Dolge . |
| 2,402,306 | 6/1946 | Turkel . |
| 2,498,692 | 2/1950 | Mains . |

(List continued on next page.)

FOREIGN PATENT DOCUMENTS

WO 99/44656   9/1999   (WO) .

OTHER PUBLICATIONS

Anonymous, "NOGA[TM] Cardiac Navigation System," Biosense, Inc., Publication No. BC0299003–1 (February 1999).

(List continued on next page.)

*Primary Examiner*—Angela D. Sykes
*Assistant Examiner*—Patricia Bianco
(74) *Attorney, Agent, or Firm*—Leydig, Voit & Mayer, Ltd.

(57) ABSTRACT

The invention is directed to a device and method for delivering a therapeutic substance (64) to a bodily tissue in a minimally invasive manner. The device includes an elongate flexible tubular member (12) having a proximal end (14) and a distal end (16). A control lever (50) is provided for enabling the distal end (16) of the tubular member (12) to be controllably flexed in a transverse manner for positioning the distal end (16) of the tubular member (12) proximate to the bodily tissue to be treated. A hollow needle (62) is disposed at the distal end (16) of the tubular member (12) for delivering the therapeutic substance (64) into the bodily tissue. A marking device (78) is also included for indicating the location where an injection has been made in the tissue. This enables the surgeon to keep track of the areas in which injections are made so that the therapeutic substance (64) may be evenly distributed over a desired area of treatment. A method for using the device is also disclosed wherein a patient's lung (120) is partially collapsed to enable access to areas of the heart (128). The therapeutic substance (64) may be injected into the patient's myocardium (138) by passing the needle (62) directly through the patient's pericardium (126). The invention is particularly useful for treatment of ischemic heart disease by gene therapy.

31 Claims, 5 Drawing Sheets

U.S. PATENT DOCUMENTS

| | | |
|---|---|---|
| 2,512,568 | 6/1950 | Saffir . |
| 2,551,902 | 5/1951 | Rieck . |
| 2,670,673 | 3/1954 | Gordon et al. . |
| 2,688,329 | 9/1954 | Wallace . |
| 2,700,385 | 1/1955 | Ortiz . |
| 2,952,256 | 9/1960 | Meader et al. . |
| 3,435,824 | 4/1969 | Gamponia . |
| 3,467,096 | 9/1969 | Horn . |
| 3,487,837 | 1/1970 | Petersen . |
| 3,530,492 | 9/1970 | Ferber . |
| 3,572,336 | 3/1971 | Hershberg . |
| 3,595,231 | 7/1971 | Pistor . |
| 3,765,420 | 10/1973 | Felczak . |
| 3,783,876 | 1/1974 | Dye . |
| 3,797,491 * | 3/1974 | Hurschman ................. 128/215 |
| 3,826,241 | 7/1974 | Bucalo . |
| 3,831,584 | 8/1974 | Bucalo . |
| 3,920,001 | 11/1975 | Edwards . |
| 3,951,132 | 4/1976 | Bucalo . |
| 3,991,767 | 11/1976 | Miller . |
| 4,150,669 | 4/1979 | Laforre . |
| 4,167,179 | 9/1979 | Kirsch . |
| 4,168,708 | 9/1979 | Lepley . |
| 4,222,380 | 9/1980 | Terayama . |
| 4,230,119 | 10/1980 | Blum . |
| 4,243,035 * | 1/1981 | Barrett ..................... 128/215 |
| 4,245,624 | 1/1981 | Komiya . |
| 4,280,508 | 7/1981 | Barrada . |
| 4,299,230 | 11/1981 | Kubota . |
| 4,356,826 | 11/1982 | Kubota . |
| 4,419,094 | 12/1983 | Patel . |
| 4,578,061 | 3/1986 | Lemelson . |
| 4,645,495 | 2/1987 | Vaillancourt . |
| 4,674,506 | 6/1987 | Alcond . |
| 4,721,109 | 1/1988 | Healey . |
| 4,753,236 | 6/1988 | Healey . |
| 4,760,847 | 8/1988 | Vaillancourt . |
| 4,787,891 | 11/1988 | Levin et al. . |
| 4,798,193 | 1/1989 | Giesy et al. . |
| 4,838,854 | 6/1989 | Kuzmanovich . |
| 4,861,336 | 8/1989 | Helzel . |
| 4,877,037 | 10/1989 | Ko et al. . |
| 4,919,653 | 4/1990 | Martinez et al. . |
| 4,932,421 | 6/1990 | Kaali et al. . |
| 4,940,458 | 7/1990 | Cohn . |
| 4,946,442 * | 8/1990 | Sanagi ..................... 604/164 |
| 4,946,463 | 8/1990 | Wright . |
| 4,966,589 | 10/1990 | Kaufman . |
| 4,976,688 | 12/1990 | Rosenblum . |
| 4,994,041 | 2/1991 | Dombrowski et al. . |
| 5,036,868 | 8/1991 | Berggren . |
| 5,037,428 | 8/1991 | Picha . |
| 5,080,104 | 1/1992 | Marks et al. . |
| 5,098,412 | 3/1992 | Shiu . |
| 5,121,750 * | 6/1992 | Katims ..................... 128/734 |
| 5,146,913 | 9/1992 | Khorsandian . |
| 5,147,307 | 9/1992 | Gluck . |
| 5,192,270 | 3/1993 | Carswell, Jr. . |
| 5,192,289 | 3/1993 | Jessen . |
| 5,195,526 | 3/1993 | Michelson . |
| 5,254,088 | 10/1993 | Lundquist et al. . |
| 5,259,377 | 11/1993 | Schroeder . |
| 5,261,889 | 11/1993 | Laine et al. . |
| 5,269,754 | 12/1993 | Rydell . |
| 5,273,525 | 12/1993 | Hofmann . |
| 5,290,258 | 3/1994 | Ennis, III et al. . |
| 5,312,351 | 5/1994 | Gerrone . |
| 5,322,510 | 6/1994 | Lindner et al. . |
| 5,323,789 | 6/1994 | Berggren . |
| 5,335,670 | 8/1994 | Fishman . |
| 5,336,182 | 8/1994 | Lundquist et al. . |
| 5,354,279 | 10/1994 | Höfling . |
| 5,376,084 | 12/1994 | Bacich et al. . |
| 5,380,292 | 1/1995 | Wilson . |
| 5,395,327 | 3/1995 | Lundquist et al. . |
| 5,417,662 | 5/1995 | Hjertman et al. . |
| 5,417,683 | 5/1995 | Shiao . |
| 5,425,739 | 6/1995 | Jessen . |
| 5,441,499 * | 8/1995 | Fritzsch .................... 606/45 |
| 5,464,395 | 11/1995 | Faxon et al. . |
| 5,478,315 | 12/1995 | Brothers et al. . |
| 5,478,330 | 12/1995 | Imran et al. . |
| 5,520,650 | 5/1996 | Zadini et al. . |
| 5,522,815 | 6/1996 | Durgin, Jr. et al. . |
| 5,531,686 | 7/1996 | Lundquist et al. . |
| 5,536,251 | 7/1996 | Evard et al. . |
| 5,569,217 * | 10/1996 | Luther ..................... 604/523 |
| 5,569,237 | 10/1996 | Beckenstein . |
| 5,611,778 | 3/1997 | Brinon . |
| 5,673,704 * | 10/1997 | Marchlinski et al. ........... 607/122 |
| 5,674,197 | 10/1997 | Van Muiden et al. . |
| 5,713,890 | 2/1998 | Chasan . |
| 5,810,757 | 9/1998 | Sweezer, Jr. et al. . |
| 5,820,591 | 10/1998 | Thompson et al. . |
| 5,820,592 * | 10/1998 | Hammerslag ................. 604/95 |
| 5,827,216 * | 10/1998 | Igo et al. ..................... 604/21 |
| 5,845,646 | 12/1998 | Lemelson . |
| 5,846,225 | 12/1998 | Rosengart et al. . |
| 5,868,764 | 2/1999 | Rosengart . |
| 5,882,331 | 3/1999 | Sasaki . |
| 5,910,133 * | 6/1999 | Gould ..................... 604/164 |
| 5,911,701 * | 6/1999 | Miller et al. ................. 604/22 |
| 5,931,810 * | 8/1999 | Grabek ..................... 604/51 |
| 5,989,274 * | 11/1999 | Davison et al. ............... 606/169 |
| 5,997,509 * | 12/1999 | Rosengart et al. ............. 604/164 |

Ben–Haim et al., *Nature Med.*, 2(12), 1393–1395 (December 1996).

Flynn et al., Abstract from *Biotechniques*, 28(3), 470–470 and 475–476 (March 2000). [http://www.ncbi.nlm.n.h-.gov:80/enteez/query.fcgi?cmd–Retrieve&db=PubMed&List–uids=10723559&dopt=Abstract].

Fuchs et al., *Suppl. to J. Am. Coll. Cardiol.*, 33(2 Suppl. A), 371A, Abstract 849–5 (February 1999).

OTHER PUBLICATIONS

Gepstein et al., *Circulation*, 96(11), 4036–4043 (Dec. 2, 1997).

Gepstein et al., *Circulation*, 96(10), 3672–3680 (Nov. 18, 1997).

Gepstein et al., *Circulation*, 95(6), 1611–1622 (Mar. 11997).

Kornowski et al., *Circulation*, 102, 1120–1125 (Sep. 5, 2000).

Kornowski et al., *J. Am. Coll. Cardiol.*, 35(4) 1031–1039 (Mar. 15, 2000).

Karnowski et al., *Circulation*, 101(4), 454–458 (Feb. 1, 2000).

Kornowski et al., Abstract from *Catheter Cardiovas. Interv.*, 48(4), 447–453 (December 1999). [http://www.ncbi.nlm.ni-h.gov:80/entrez/query,fegi?cmd=Retrieve&db=PubMed&listuids=10559830&dopt=Abstract].

Kornowski et al., Abstract from *J. Invasive Cardiol.*, 11(6)329–336 (June 1999).

Kornowski et al., *Suppl. to J. Am. Coll. Cardiol.*, 33 (2, Suppl. A), 334A, Abstract 1035–1039 (February 1999).

Kornowski et al., *Circulation*, 98(18), 1837–1841 (Nov. 3, 1998).

Kornowski et al., *Int. J. Cardiovasc. Interv.*, 1(1), 3–9 (August 1998).

Kornowski et al., *Left Ventricular Electromechanical Mapping: Endomyocardial Diagnosis and Therapy*, $2^{nd}$ ed. (Cardiovascular Research Foundation, Washington, DC 1998).

Schwartz, "Therapeutic Angiogenesis Overview," Biosense, Inc., Publication No. BC0299004–1 (February 1999).

Shah et al., *Circulation*, 96(11) 3904–3912 (Dec. 2, 1997).

Shpun et al., *Circulation*, 96(6), 2016–2021 (Sep. 16, 1997).

Thambar et al., *Suppl. to Circulation*, 100(18, Suppl. I), I–23, Abstract 115 (Nov. 2, 1999).

Vale et al., *Circulation*, 102(9), 965–974 (Aug. 29, 2000).

* cited by examiner

_MINIMALLY INVASIVE GENE THERAPY DELIVERY AND METHOD_

RELATED APPLICATIONS

This application is a continuation-in-part of U.S. Ser. No. 09/035,892, filed Mar. 6, 1998, now U.S. Pat. No. 5,997,509, entitled "Minimally Invasive Gene Therapy Delivery Device And Method."

FIELD OF THE INVENTION

This invention embodies a therapeutic medical device and a method of treatment. In particular, the device is suitable for treating target tissue of a patient by injection of predetermined quantities of a substance into bodily tissue at successive locations within the patient's body. One particular application to which this invention may be applied is the delivery of therapeutic substances to the heart to induce angiogenesis for improving blood flow in heart tissue.

BACKGROUND OF THE INVENTION

Despite the recent advances in the treatment of ischemic heart disease, there still exist a significant number of patients for whom conventional therapies such as angioplasty and coronary bypass surgery are not feasible options. In particular, alternative therapies are required for patients in a number of circumstances. For example, patients with diffuse small vessel coronary artery disease cannot be treated by conventional coronary bypass surgery because of the small size and large number of diseased vessel segments. In other patients, re-occlusion of a diseased vessel may occur despite multiple angioplastic procedures or bypass surgeries. Accordingly, the need exists for alternative intervention methods.

One promising alternative treatment for ischemic heart disease is the delivery of angiogenesis-promoting substances to the heart tissue to induce angiogenesis. Angiogenesis is a complex biological process that results in the growth of new blood vessels within tissue. Angiogenesis is an essential process common to several normal and pathologic conditions including embryologic development, wound healing, development of neoplasms, and the like.

Angiogenesis has also been induced in heart tissue for re-perfusion of tissue compromised by myocardial ischemia. Several growth factors have been identified and are intimately involved in initiating and promoting angiogenesis in tissue within a living body. These growth factors are typically proteins which stimulate endothelial cell reproduction in the target tissue. The tissue must be exposed to the growth factors for a period of time, i.e., a number of days. In addition, the growth factor should be limited to the target tissue so that angiogenesis is not induced in sensitive non-diseased organs, such as the retina, or in occult tumors.

The growth factor may be delivered to the target tissue through the use of indwelling catheters over a period of time. However, a preferred method of delivering the growth factor is in the form of gene transfer by a replication deficient adenoviral vector. Under this method, a quantity of adenovirus having the desired genetic component is delivered to the treatment area by injection in solution.

In the past, an open-chest procedure has been used to deliver the treatment solution. According to this procedure, the patient's chest is opened surgically to expose the heart. The solution containing the adenovirus is then delivered to the heart tissue by using a syringe to make a number of injections in a grid-like pattern, with the surgeon keeping track of the location of each injection. Once injected, the adenovirus causes the cells in the target tissue to express the desired growth factor protein, and this protein expression from the treated cells will continue for the desired period of time. Previous studies have shown the feasibility and efficacy of safe, sustained, and localized expression of angiogenesis-promoting growth factors utilizing adenoviral-mediated gene transfer therapy.

It is desirable, however, to be able to provide the above-described therapy without the necessity of performing open-chest surgery on the patient. Accordingly, the present invention sets forth an apparatus and method for providing gene therapy treatment to the heart or other internal organs in a minimally invasive manner. The present invention also provides an apparatus and method for delivering angiogenesis-promoting substances to an area of diseased tissue with greater ease and efficiency, and with reduced trauma and recovery time for the patient. Accordingly, the subject invention could be potentially helpful to hundreds of thousands of patients with severe ischemic heart disease who are not candidates for surgical bypass or balloon angioplasty.

SUMMARY OF THE INVENTION

The present invention embodies a novel, minimally invasive injection apparatus and method. The invention is useful, for example, in gene transfer therapy for injecting an angiogenesis-promoting factor into living tissue, such as into the myocardium. The injection device includes an elongate flexible tubular body having a proximal end and a distal end. A hollow needle is mounted on the distal end of the tubular body. The needle is capable of penetrating the target tissue for delivering a therapeutic substance to the tissue.

In addition, a marking device and a method of marking are preferably provided. The marking device may result in a physical indication that may be viewed thoracoscopically, as would be effected, for example, by including a dye or the like in the injected substance, or other physical marking the location of the injection. In the illustrated embodiment, the marking device is in the form of a marking element mounted on a platen on the distal end of the tubular member. When the therapeutic substance is delivered to the bodily tissue, the marking element leaves a discernible mark on the target tissue so that the surgeon may keep track of which areas of tissue have been treated by viewing though a thoracoscope, or by other means. Preferably, a stop is provided which is spaced in from the distal tip of the needle. The stop regulates the distance to which the needle may penetrate the target tissue. In an illustrated embodiment, the platen and needle are fixed relative to each other so that the platen, by contacting the tissue surface, acts as a stop and ensures that the needle penetrates the target tissue to the same depth with each injection.

Alternate methods of marking and marking devices may result in markers or indications that may be detected thoracoscopically, ultrasonographically, radiographically, or fluoroscopically, as, for example, by x-ray or CAT scan, or by other three-dimensional imaging systems. Virtual marking or mapping may likewise be utilized. With electrocardiographic marking, as by ECG, an electrode preferably is provided at the end of the needle, while the remainder of the device is insulated.

A control apparatus may also be included with the device for controllably positioning the distal end of the tubular member to facilitate proper positioning and insertion of the needle. Furthermore, a metering device may also be included for controlling the amount of therapeutic substance injected at each successive injection site.

Under the method of the invention, a therapeutic substance may be injected into living tissue successively at a plurality of locations inside the body in a minimally invasive manner. The injections may be made for a variety of purposes in a variety of bodily tissues. However, the present invention is especially suitable for delivering gene therapy to the heart. In particular, an angiogenesis-promoting factor may be introduced into myocardial territories in predetermined quantities at a plurality of points to induce the growth of bypass vessels which may allow the bridging of narrowed or occluded coronary vessels. The treatment may also be used to induce the growth of new vessels in myocardial territories poorly supplied by the native coronary vasculature. The treatment method may also be used to deliver therapeutic substances to other bodily tissues in a minimally invasive manner.

Under an additional method of the invention, a patient's lung may be partially collapsed by the introduction of gas into the patient's thoracic cavity. This enlarges the working area for injection of the therapeutic substance and increases access to heart tissue. The delivery of the therapeutic substance to the myocardium may be made transpericardially, rather than from within the pericardium. An electrode may be located on the distal end of the hollow needle, and connected to an ECG, for determining when the needle has penetrated the patient's myocardium. Penetration of the myocardium by the needle will show as a current injury on the ECG. Following delivery of the therapeutic substance by one or more injections in the manner described above, a plurality of percardiotomies are formed in the pericardium using a pericardiotomy device. This permits drainage of any pericardial effusions. This entire procedure may be performed with the patient conscious and without general anesthetic.

The multiple applications can be 2, 3, 4, 5, or more applications, preferably 5 or more applications, more preferably 8 or more applications, and most preferably at least 10 (e.g., 10, 15, or 20) applications. Multiple applications provide an advantage over single applications in that they can be manipulated by such parameters as a specific geometry defined by the location on the target tissue where each application is administered. The administration of a single dose of the angiogenic vector via multiple applications can be better controlled, and the effectiveness with which any given dose is administered can be maximized. In this way, too, the undesirable effects associated with administration of a single point application of a large dose can be minimized.

The specific geometry of the multiple applications is defined by the location on the target tissue, either in two or three-dimensional space, where each application of the angiogenic vector is administered. The multiple applications preferably are spaced such that the points of application are separated by up to about 4 cm (e.g., about 0.5–4 cm), more preferably up to about 3 cm (e.g., about 1–3 cm), and most preferably up to about 2 cm (e.g., about 1–2 cm). With respect to the specific geometry of the multiple applications in two-dimensional space, the specific geometry is defined by a plane (i.e., a cross-section of the target tissue) in which the multiple applications lie. The plane defined by the multiple applications can lie at a constant distance from the surface of the target tissue (i.e., substantially parallel to the surface of the target tissue), the depth of the plane, or, alternatively, the plane can lie at an angle with respect to the surface of the target tissue. Preferably, a single application will be administered for about every 0.5–15 $cm^2$ of the plane, more preferably for about every 1–12 $cm^2$ of the plane, and most preferably for about every 1.5–7 $cm^2$ of the plane. The depth of the plane is preferably about 1–10 mm, more preferably about 2–7 mm, and most preferably about 3–5 mm. In three-dimensional space, a single application preferably is administered for up to about 50 $cm^3$ (e.g., about 0.5–50 $cm^3$) of target tissue, more preferably for up to about 35 $cm^3$ (e.g., about 1–35 $cm^3$) of target tissue, and most preferably for up to about 15 $cm^3$ (e.g., about 3–15 $cm^3$) of target tissue. Furthermore, the multiple applications can define any suitable pattern or specific geometry. Therefore, for example, in two-dimensional space, the multiple applications can define a square whereas in three-dimensional space the multiple applications can define a cube.

Another parameter of the multiple applications which can be manipulated is the time differential between each application. Preferably, each of the multiple applications is administered within about 10 minutes (e.g., about 0.5–10 minutes) of each other, more preferably within about 8 minutes (e.g., about 0.5–8 minutes) of each other, and even more preferably within about 6 minutes (e.g., about 1–6 minutes) of each other. Most preferably, all of the multiple applications of the single dose are administered within the aforesaid time frames. Optimally, each of the multiple applications is administered substantially simultaneously.

By manipulating both the specific geometry and the time differentials of the multiple applications, the induction of angiogenesis in non-targeted tissue can be minimized. A method of multiple site delivery of adenoviral vector for the induction of angiogenesis, and a gene transfer therapy delivery device and method are disclosed, respectively, in PCT Application PCT/US98/01638, which designates the United States, and U.S. Pat. No. 5,846,225, both of which are hereby specifically incorporated by reference.

DESCRIPTION OF THE PREFERRED EMBODIMENT

Figure 1:
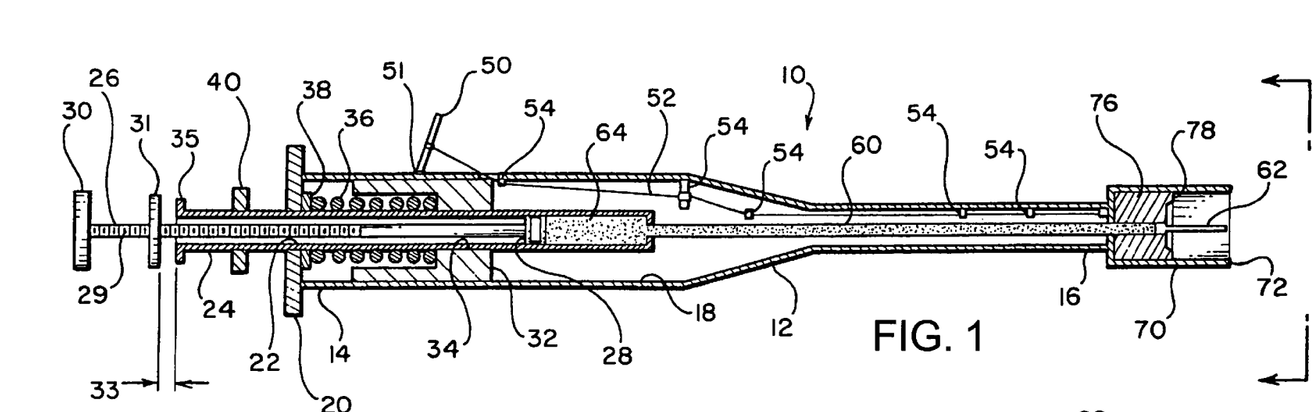
FIG. 1 is an enlarged cross-section elevation view of the delivery device of the present invention.
Figure 2:
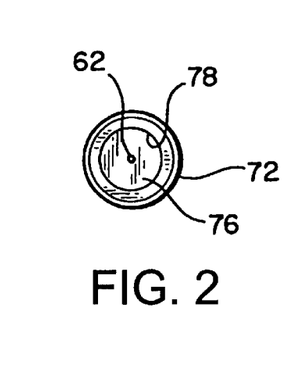
FIG. 2 illustrates an end view of the device of FIG. 1 as taken along line 2—2.

The invention is directed to a method and apparatus for delivering therapeutic treatment to body tissues. The apparatus includes a delivery device 10, as illustrated in FIGS. 1 and 2, capable of injecting a therapeutic substance into bodily tissue through a minimally invasive method. Device 10 may be inserted through a thoracoscopic port (not shown), giving thoracoscopic access to the patient's heart or other tissue. The device may advantageously be used to inject a substance in a grid-like or other pattern so that by making successive injections of a predetermined quantity of substance having a predictable diffusion mobility, an entire area of tissue can be treated.

Delivery device 10 includes an elongate flexible tubular member 12 having a proximal end 14 and a distal end 16. Tubular member 12 is constructed of a flexible material such as polyurethane, polyvinyl chloride, polyethylene, or other suitable flexible biocompatible materials. Tubular member 12 includes a lumen 18 which passes from proximal end 14 to distal end 16, and which has a generally circular cross-section. A cap 20 is mounted on the proximal end 14 of tubular member 12, and includes a circular hole 22 to allow passage of a syringe 24. Syringe 24 includes a cylindrical body having a plunger shaft 26 and a plunger 28 slidably mounted therein. Plunger 28 is mounted on the distal end of plunger shaft 26, and a plunger thumb button 30 is mounted on the proximal end of plunger shaft 26.

Plunger shaft 26 may include screw threads or other gradations 29 formed along its length. A plunger stop 31 is movably mounted on plunger shaft 26 and positionable at a predetermined distance 33 from the proximal end 35 of syringe 24. Plunger stop 31 ensures that when plunger 28 is depressed, only a predetermined amount of therapeutic substance is dispensed from syringe 24. Following delivery of the substance, plunger stop 31 is reset by moving proximally back along plunger shaft 26 of the predetermined distance 33. This may be accomplished by turning plunger stop 31 back along threads 29 or the like. Syringe 24 is thereby set to deliver the next predetermined dose of therapeutic substance at the next injection location. Other devices for metering the amount of therapeutic substance delivered may also be used. For example, a ratchet mechanism (not shown) may be incorporated into the syringe for enabling consistent delivery of successive constant amounts of therapeutic substance in an aliquot manner. The physician depresses plunger button 30 until the ratchet mechanism stops the forward motion at a predetermined distance. The ratchet mechanism would then reset to enable to the plunger to be depressed an additional predetermined distance, and so forth.

A cylindrical support 32 is located within lumen 18 of tubular member 12. Cylindrical support 32 has a circular opening 34 therethrough for receiving and supporting syringe 24. Syringe 24 is able to slide axially within circular hold 22 in cap 20 and circular opening 34 in cylindrical support 32. A spring 36 is fixedly mounted concentrically on syringe 24 between cylindrical support 32 and annular spring stop 38. Spring stop 38 is a disk-shaped member mounted on syringe 24, and is fixed to syringe 24 so that it moves axially as syringe 24 is moved axially. A second stop member 40 is fixedly mounted on syringe 24 proximal of cap 20. Second stop member 40 is also a disk-shaped member which is fixed to the exterior of syringe 24. Second stop member 40 prevents syringe 24 from being advanced too far into tubular body 12, when syringe 24 is moved axially in the distal direction relative to tubular body 12.

In order to control the transverse movement of the device 10 within the patient's body, a control apparatus is provided. In this regard, a control lever 50 is mounted on the side of tubular body 12 for controlling the position of distal end 16 of tubular body 12. Control lever 50 is pivotally mounted to tubular body 12 at pivot points 51, and is connected to a control wire 52 which is connected to the distal end 16 of tubular body 12 in an offset manner. Control wire 52 may be retained within eyelets 54 located within lumen 18 of tubular body 12, or may be retained within a separate lumen (not shown), or by other means, as is known in the art.

Figure 3:
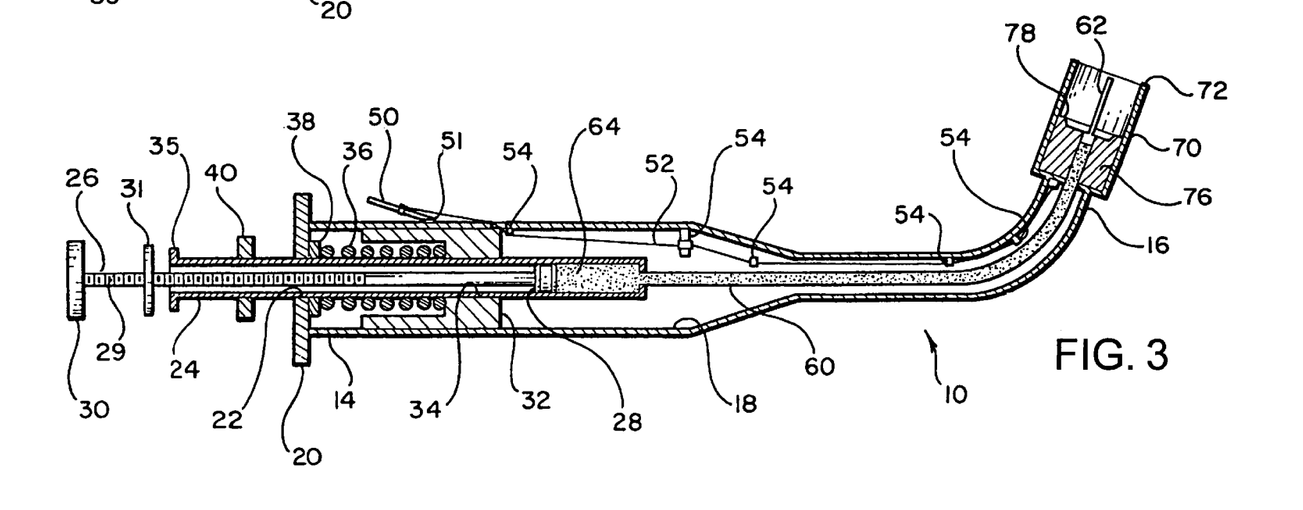
FIG. 3 illustrates the delivery device of FIG. 1 with the distal portion flexed transversely.

As illustrated in FIG. 3, when control lever 50 is pulled in the proximal direction, it may be seen that control wire 52 will pull on the distal end 16 of tubular body 12. This causes tubular body 12 to bend or flex transversely so that distal end 16 is disposed in an oblique direction relative to the major axis of tubular body 12. An adjustment mechanism (not shown) may be included for holding control lever 50 in a particular desired position. In addition, other control devices may be substituted for lever 50, as is known in the art. For example, a threaded knob (not shown) may be used in place of lever 50, with the knob being turned in one direction to pull on control wire 52, and being turned in the other direction to release tension on control wire 52.

A flexible tube 60 is connected to the distal end of syringe 24, in fluid communication with syringe 24. The distal end of flexible tube 60 is connected to a hollow needle 62 of the hypodermic type. A therapeutic substance 64 contained within syringe 24 may be expelled through needle 62 by pressing syringe plunger button 30. This forces the therapeutic substance from syringe 24, through flexible tube 60, and out the distal end of needle 62. It will be appreciated that the flexible tube 60 and needle 62 may be in the form of an elgonated needle, such as is disclosed in U.S. application Ser. No. 09/368,886, filed Aug. 5, 1999, which is hereby incorporated by reference.

To prevent needle 62 from accidentally penetrating non-target tissue during positioning of device 10, a cup 70 is mounted on the distal end 16 of tubular body 12 to serve as a guard. Cup 70 is a hollow cylindrical member, and includes a wall having a distal edge 72 which extends at least as far as the tip of needle 62 when needle 62 is in the retracted position, as illustrated in FIGS. 1 and 3. Accordingly, as long as needle 62 is retracted, cup 70 will prevent needle 62 from contacting non-target areas during placement of device 10 within a patient.

In order to achieve desired placement and spacing of successive injections, the device 10 is provided with a marking device whereby the cardiologist may view the location of previous injection sites and placement patterns. The marking device may be of any appropriate type.

Those skilled in the art will appreciate that the marking device may utilize a marker that may be detected by any appropriate method, including, but not limited to visually, thoracoscopically, virtually, fluoroscopically, radiographically, electrocardiographically, or ultrasonographically, or, in cardiac tissue in particular, echocardiographically. By way of example, one such visually or thoracoscopically viewable marker of the injection site may be a mechanically marking element such as a suture, clip, button, or disk which would be applied via an automated system. Further, visually or thoracoscopically viewable marking substances such as dyes may be used to mark injection sites and placement patterns. Similarly, echodense substances may be used to mark sites which are viewed echographically, while radiographic contrasting agents or fluoroscopic dyes allow for the use of fluoroscopic, radiographic or other three-dimensional imaging system viewing of markings and placement patterns. Such substances may be included in the injected substance itself, separately injected, or used to mark the surface of the tissue substantially adjacent in the injection site.

One such device and method of marking the surface of the tissue is illustrated in FIGS. 1–7. In this embodiment, the platen 76 includes a raised marking ring 78 on its distal outer side for making a discernible mark on the tissue surface when needle 62 is inserted into the tissue. Marking ring 78 is a raised ring that concentrically encircles needle 62. Ring 78 may be constructed of an absorbent polymeric substance saturated with a visual dye, such as methylene blue. When ring 78 is pressed against tissue, ring 78 will leave a discernible ring-shaped mark on the tissue. The ring-shaped mark will indicate to the surgeon which area of tissue has already received an injection of therapeutic substance 64.

Alternately, known virtual marking apparatus may be utilized. In this way, the needle 62 may be coupled to a computer such that each movement of the needle may be recorded and virtually marked on a computer screen. While any appropriate mapping system may be utilized, one such endocardographical mapping system that may be particularly appropriate is the NOGA System, which comprises an EKG type monitoring system sensitive to electrical activity of the myocardium.

Figures 4, 5:
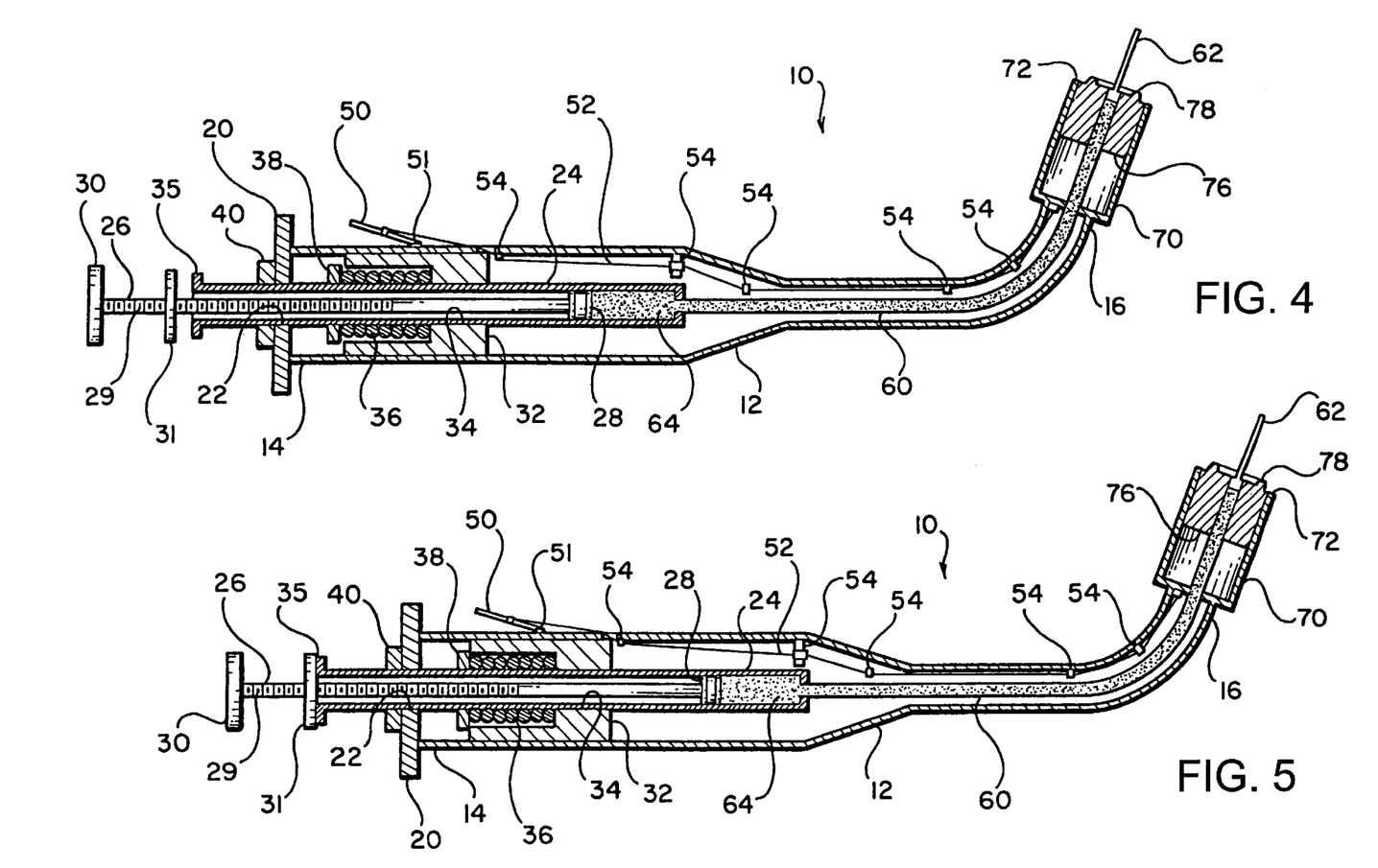
FIG. 4 illustrates the delivery device of FIG. 3 with the needle and marking platen extended.
FIG. 5 illustrates the delivery device of FIG. 4 following injection of a portion of the therapeutic substance.

Returning now to the drawings, as illustrated in FIG. 4, syringe 24 may be moved axially forward in the distal direction relative to tubular body 12 to extend needle 22 and platen 76. Syringe 24 is moved forward against the bias of spring 36, thereby compressing spring 36. As syringe 24 is moved distally, flexible tube 60, needle 62 and platen 76 also move distally so that needle 62 and marking ring 78 extend beyond the distal edge 72 of cup 70. Second stop member 40 is fixed on syringe 24 in a location which ensures that when second stop member 40 comes into contact with cap 18, needle 62 and marking ring 78 are properly extended beyond the distal edge 72 of cup 70. Syringe 24 may be retained in the forward position by a latch (not shown), by the surgeon's hand, or by other means. Upon release of syringe 24, spring 36 will force syringe 24 back in the proximal direction, thereby retracting needle 62 and platen 76 back into cup 70. This enables needle 62 to properly retract following each injection so that needle 62 does not accidentally penetrate non-target areas.

Figure 6:
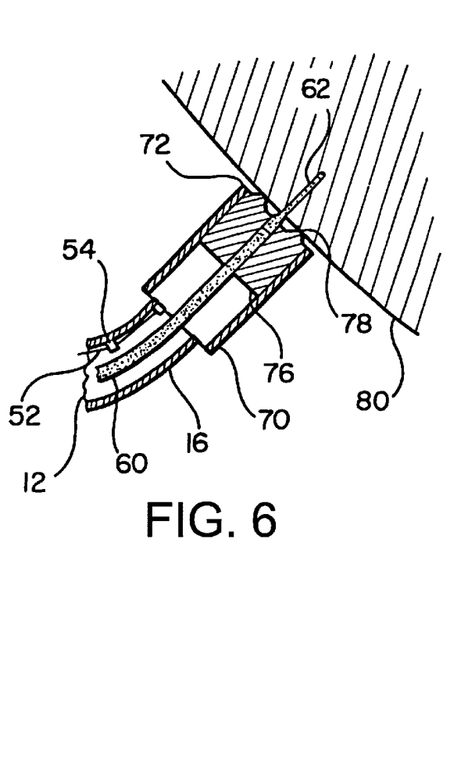
FIG. 6 illustrates the delivery device of FIG. 5 during injection of the therapeutic substance into tissue.

Flexible tube 60 is able to flex in the transverse direction, as illustrated in FIGS. 3–5, but has sufficient column strength so that as syringe 24 is moved forward, flexible tube 60 will push platen 76 and needle 62 distally so that needle 62 is able to penetrate target tissue 80, as illustrated in FIG. 6. Suitable materials for use as flexible tube 60 include hypotube, polyvinyl chloride tube, or other sufficiently stiff biocompatible materials. In addition, to prevent tube 60 from buckling, the clearance between flexible tube 60 and lumen wall 18 of tubular body 12 may be small enough so that lumen wall 18 will support flexible tube 60.

Figure 7:
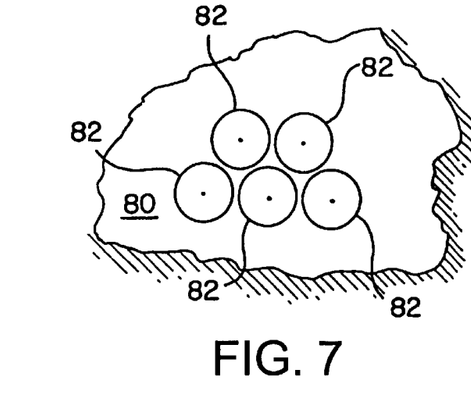
FIG. 7 illustrates a typical injection pattern for delivery of a therapeutic substance to an area of tissue.

As illustrated in FIG. 6, once needle 62 has penetrated the target tissue 80, marking ring 78 on platen 76 will come into contact with the surface of tissue 80. Then, as illustrated in FIG. 5, plunger thumb button 30 is depressed so that a quantity of therapeutic substance 64 is injection into tissue 80. Plunger stop 31 contacts the proximal end 35 of syringe 24, thereby ensuring that a predetermined dose of therapeutic substance is delivered. Needle 62 is then withdrawn from target tissue 80, and marking ring 78 leaves a discernible mark on target tissue 80. The distal end of device 10 is then repositioned to the next target site for the next injection. In this manner, an area of tissue 80 may be treated with therapeutic substance 64 without overlap. A typical grid-like pattern for such treatment is illustrated in FIG. 7, showing a plurality of ring-shaped marks 82 formed on the surface of tissue 80 by marking ring 78 during successive injections.

When determining the amount of solution to be expelled from needle 62, factors taken into consideration include the proximity of the injection sites to each other and the mobility of the solution within tissue 80. To simplify the process, the area covered by ring 78 is preferably the same as the estimated dispersion area of the predetermined injection quantity of therapeutic substance within the tissue. In addition, the amount of fluid delivered will vary in correspondence with the type of treatment being administered. Accordingly, the spacing of the injection sites, the volume of therapeutic substance to be delivered, the mobility of the therapeutic substance in tissue, the desired area of coverage, and the depth of delivery are all factors which may be taken into account when determining the spacing of the injection pattern. The geometric pattern shown in FIG. 7 provides diffuse coverage with minimal overlap, and with minimal uncovered areas within the overall geometry.

The distance which needle 62 extends beyond platen 76 may be adjusted from patient to patient and for particular uses by using needles of different length. One reason for controlling the depth of needle penetration when treating ischemic heart disease is to ensure that the needle tip is located sub-epicardially, e.g., at approximately 5 mm depth. Platen 76 ensures that the needle tip is always located at the same depth within the tissue during each injection. This ensures a more uniform delivery of the therapeutic substance over the entire treatment area. Of course for some treatment purposes, differing amounts of fluid could be delivered to different areas of tissue by controlling the quantity of fluid dispensed from the syringe during each injection.

Additional features of device 10 may include a fiber optic light source (not shown) located at the distal tip of device 10. The light source may emit from platen 76, from the edge of cup 70, or from other locations. The light source would aid in visualization of the target tissue prior to injection, and also in visual perception of the visually marked injection sites, which in the illustrated embodiment include the ring-shaped markings 82, following injection and contact of the target tissue with marking ring 78.

While it will be apparent that the particular dimensions of device 10 may vary for particular applications, the preferred embodiment of device 10 is between 12 and 18 inches in overall length. The maximum diameter of the preferred embodiment is less than 12 mm for the portion of device 10 which is inserted into the patient. This enables device 10 to fit through a 12 or 15 mm thoracoscopic port.

The device of the subject invention may be used to inject a variety of fluids into tissue for a variety of therapeutic reasons. In one preferred method of the present invention, the delivery device is used to deliver an angiogenesis-promoting compound to a portion of the myocardial wall that is suffering from insufficient blood supply. The treatment may be used independently for promoting the growth of new blood vessels, or may be used in conjunction with other procedures such as angioplasty, bypass surgery, transmyocardial revascularization, or the like. The device of the subject invention enables quick, precise, and effective delivery of controlled quantities of the angiogenesis-promoting substance over a desired coverage area with minimal overlap.

Several growth factors have been identified and are intimately involved in initiating and promoting angiogenesis. Included in this family of angiogenic growth factors are acidic fibroblast growth factor ("aFGF"), basic fibroblast growth factor ("bFGF"), and vascular endothelial growth factor ("VEGF"). VEGF in particular has been shown to be capable of promoting angiogenesis in several models of chronic ischemia, including ischemic myocardium in both porcine and canine experiments, and also in the ischemic hind limbs of lab animals.

A preferred method of delivering VEGF is in the form of cDNA or gene coding in a replication-deficient adenoviral ("Ad") vector. A quantity of adenovirus carrying the desired genetic component is delivered to the treatment area by injection in solution. Previous studies have shown the feasibility and efficacy of safe, sustained, and localized expression of VEGF utilizing adenoviral mediated gene transfer therapy.

Thus, under one aspect of the present invention, a predetermined quantity of angiogenesis-promoting factor is loaded into syringe 24, and plunger stop 31 is set at a predetermined distance 33 for dispensing 0.1 cc of the angiogenesis-promoting factor. The patient's heart is accessed via a thoracotomy incision of 7 cm or less, or, in a thoracoscopic approach, via a 15 mm port. Additional ports may be used to provide visualization and manipulation of tissue. A pericardial incision is formed, and stay sutures are emplaced. With the heart appropriately positioned, using retracting devices or the like, cup 76 of device 10 is placed adjacent the myocardial wall. Needle 62 is then extended to penetrate the target tissue until ring 78 or other stop contacts the tissue. Plunger 28 is then depressed until plunger stop 31 contacts the proximal end 35 of syringe 24 to deliver the angiogenesis-promoting factor to the ischemic myocardial tissue in the manner described above. Needle 62 is then withdrawn and repositioned at the next target site. Plunger stop 31 is moved back along plunger rod 26 a predetermined distance 33 for dispensing a second dose of the angiogenesis-promoting substance.

Additional areas of tissue are injected until the entire target area has been treated. A typical procedure may comprise 10 to 30 injections of 0.1 cc each for a total of 1.0 cc of angiogenesis-promoting substance being delivered over a 10 $cm^2$ area. Of course, specific amounts of substance delivered, and the area covered will be dictated by the specific treatment being implemented, and the above specifics are not intended to be limiting and are only given for describing the preferred best mode of treatment.

Following injection into the tissue, the angiogenesis-promoting factor initiates the complex process of angiogenesis in the treated tissue, thereby inducing the growth of new blood vessels. This treatment is of benefit to heart tissue in which the existing blood vessels are clogged or narrowed, and is also of benefit to heart tissue which is poorly supplied by the native coronary vasculature for congenital reasons.

Under an additional method of use for the present invention, a patient's lung may be partially collapsed to provide greater access to heart tissue. This advances one of the primary goals of the invention, which is to deliver a gene therapy substance to a patient in a highly non-invasive manner. Thus, the invention may be used by making only small incisions in a patient's chest, and may be performed without general anesthesia. Normally, any operation having an open communication with the thoracic cavity will result in the collapse of the lungs because of loss of negative intrathoracic pressure that allows the lungs to remain expanded by external atmospheric pressure. An opening into the thoracic space results in an equalization of atmospheric pressure with the pressure inside the thoracic cavity, leaving the lungs unsupported. Conventional thoracic surgery utilizes general anesthesia, tracheal intubation, and positive pressure ventilation to allow lung inflation and ventilation when the thoracic cavity is opened. More recently, a double-lumen endotracheal tube has been used which isolates the two lungs, enabling one lung to be ventilated while the other lung is collapsed to enable it to be operated on.

The requirements for accessing the pericardium or myocardium to deliver therapeutic substance 64 is to have a sufficiently large operating field or "window" in the thoracic cavity to allow visualization of instrumented manipulation of the pericardium while maintaining normal ventilation and without using general anesthesia. While patients can tolerate complete collapse of one lung for short periods of time, complete collapse of a lung for extended periods of time is potentially discomforting and possibly dangerous. The goal therefore is to provide some working space within the thoracic cavity while maintaining normal negative pressure ventilation, and, thus, a sealed chest wall.

The approach of the present invention accomplishes this by mimicking the normal pathophysiology of partial pneumothorax. A patient's lung is partially collapsed by introducing air or other gas into the thoracic space. Instrumentation is then introduced via airtight ports and transpericardial delivery of the therapeutic substance is performance. The advantage of this approach is that the partial lung collapse provides space in the thoracic cavity in which to access the heart tissue, while avoiding the problem of having to manipulate instruments around a fully expanded lung during the therapeutic procedure. With the chest wall sealed, the partially expanded portion of the lung will be ventilated according to normal chest wall dynamics, thus avoiding the deleterious effects of total lung collapse.

Figure 8:
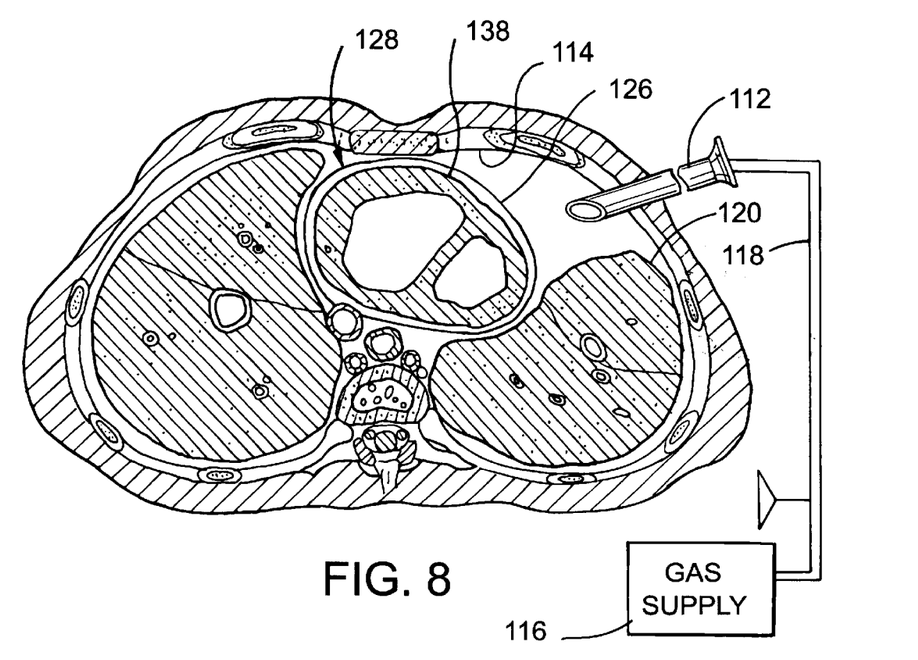
FIG. 8 illustrates a cross-section of a patient's thorax showing the introduction of a trocar to collapse a lung under a method of the invention.

In practice, as illustrated in FIG. 8, a local anesthetic is administered to the patient, and a trocar 112 is introduced into the chest wall at approximately the sixth intercostal space in the anterior axillary line. Trocar 112 is of a conventional design, and has a self-sealing membrane (not shown) that can be kept airtight, but which will also permit passage of instruments, such as an endoscopic camera, retractors, delivery device 10, or the like.

Figure 9:
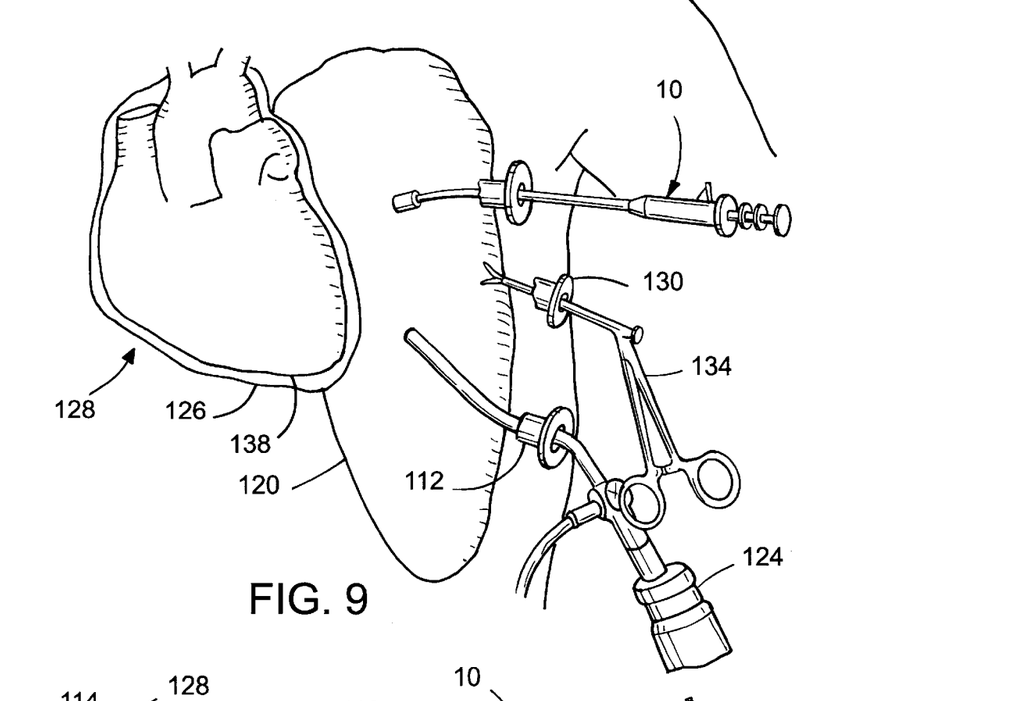
FIG. 9 illustrates a plan view of the patient during performance of a method of the invention.

Once the trocar 112 is in place, approximately 1500 ml of $CO_2$ gas is introduced into the thoracic cavity 114 of the patient through the seal of trocar 112. The gas is delivered from a gas supply 116 through a delivery line 118 to trocar 112. The introduction of the gas into the patient's thoracic cavity 114 partially collapses one of the patient's lungs 120. During the procedure, the patient is kept in a slightly head-down position to allow accumulation of the gas at the lower portion of the thoracic cavity 114, which is generally the desired work space. Following introduction of the gas, gas delivery line 118 is removed, and a conventional endoscopic camera 124 is introduced through trocar 112, as illustrated in FIG. 9. Endoscopic camera 124 is used to visualize the pericardium 126 of the patient's heart 128, and the surrounding work space.

A second self-sealing trocar 130 is then introduced through the patient's chest to also access the patient's thoracic cavity 114. A conventional thoracoscopic lung retractor 134 is then introduced through second trocar 130, and is used to further retract the collapsed portion of lung 120 away from the heart 128. Retractor 130 may be the grasping type of retractor illustrated, or may be a mechanically expandable retractor, an inflatable retractor, or other type of retractor known in the art. A third self-sealing trocar 136 is then introduced to also access the patient's thoracic cavity 114. The delivery device 10 of the present invention may then be introduced through third trocar 136 to deliver therapeutic substance 64 to the myocardium 138 of the patient's heart 128.

Advantageously, the delivery of therapeutic substance 64 may take place by injection directly through the pericardium 126. This is preferred because a large number of patients who are eligible for the procedure may have already had previous open heart surgery. Accordingly, the pericardium of these patients may be ablated with scar tissue. Thus, transpericardial delivery of therapeutic substance 64 is more easily accomplished then delivering the injections from within the pericardium 126.

Figure 10:
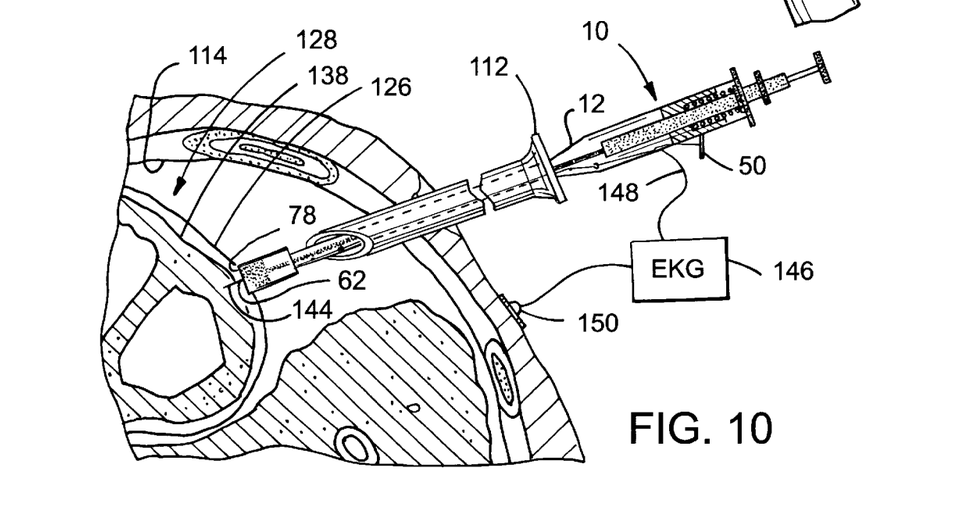
FIG. 10 illustrates an enlarged view of the thorax of FIG. 9, showing delivery of a therapeutic substance.

However, as illustrated in FIG. 10, when using transpericardial delivery, a means to determine when myocardial penetration has occurred is desirable for ensuring proper delivery of therapeutic substance 64. One such means is the inclusion of an electrode 144 at the tip of hollow needle 62. Electrode 144 may be insulated from needle 62, and located on the tip thereof, or needle 62 itself may serve as electrode 144 if needle 62 is made of a conductive substance. Electrical connection of this electrode 144 to an electrocardiograph ("ECG") 146 is made by running an electrical connector 148 along the interior length of tubular body 12 to an ECG 146 located outside the patient's body. Standard surface ECG leads 150 are applied to the patient as well. When electrode 144 enters the patient's myocardium 138, this event shows up as a current injury on ECG 146. It will be appreciated by those of skill in the art that the ECG may likewise be utilized in marking the locations of successive injections, i.e., the injection pattern.

Figure 11:
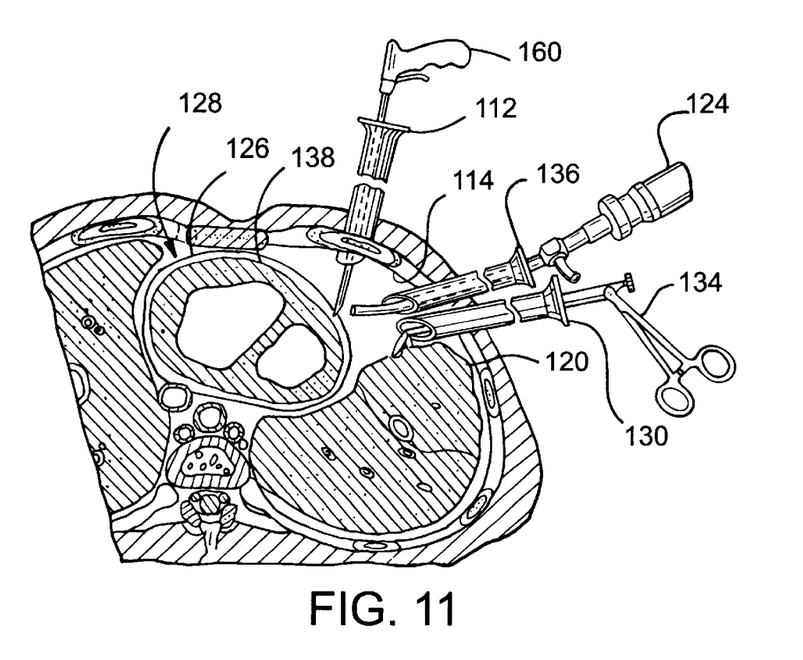
FIG. 11 illustrates the formation of pericardiotomies under a method of the invention.

Accordingly, delivery device 10 is manipulated around the pericardial surface, in the manner described above, by manipulating control lever 50. A series of injections are made, with the location of each injection being marked on pericardium 126 by marking ring 78. Eventually the entire intended area of treatment is traversed, and delivery device 10 is withdrawn through third self-sealing trocar 136. As illustrated in FIG. 11, a pericardiotomy device 160 is then introduced through third trocar 136. Pericardiotomy device 160 may be any of a number of conventional laparoscopic cutting devices capable of forming openings in pericardium 126. Pericardiotomy device 160 is used to form a series of pericardiotomies in pericardium 126 to allow drainage of potential pericardial effusions. Such effusions may be a side effect of the VEGF gene present in therapeutic substance 64. Following this procedure, pericardiotomy device 160, endoscope 124, and retractor 134 are withdrawn from trocars 112, 136, and 130, respectively. Trocars 112, 130, 136 are withdrawn in the reverse sequence of insertion. The gas is suctioned from the thoracic cavity prior to withdrawal of the final trocar. The patient is asked to take a deep breath as the last trocar is removed, and the trocar incision is sealed using purse string sutures.

It will be appreciated by those of skill in the art that under certain conditions, in particular, in re-op patients wherein a section of the collapsed lung is plastered to the heart, it may be necessary and desirable to pass the needle through the lung and the pericardium. Accordingly, the needle 62 would penetrate tissue to a greater depth, e.g., on the order of 1 to 2 cm and the stop or platen 76 would preferably be appropriately spaced from the needle tip to allow for a desired sub-epicardial depth of penetration on the order of 5 mm. Under these circumstances, it is particularly desirable to use an ECG monitoring system, i.e., provide an electrode at the needle tip in order to confirm when the needle has, in fact, penetrated the myocardium.

Thus, the present invention sets forth a method and apparatus for delivering predetermined quantities of therapeutic substance to biological tissue successively at a plurality of locations to achieve therapeutic treatment over a desired area of tissue quickly and accurately. Other uses and benefits of the disclosed present invention will be apparent to those skilled in the art. Therefore, while preferred embodiments of the invention have been described herein, it will be recognized that a variety of changes and modifications may be made without departing from the spirit of the subject invention, the scope of which is set forth in the following claims.

What is claimed is:

1. A device for making sequential injections of a therapeutic substance to bodily tissue wherein a portion of the device is inserted into a cavity within a body of a patient prior to injection, said device comprising:

an elongate flexible tubular member having a proximal end and a distal end;

a hollow needle mounted on said distal end of said tubular member, said needle being capable of penetrating the bodily tissue for delivering a therapeutic substance to the tissue; and a marking device having at least a portion substantially disposed adjacent said distal end, said marking device leaving a discernible indication where the therapeutic substance has been delivered to the bodily tissue such that the discernible indication may be viewed relative to previous and/or subsequent discernible indications.

2. The device of claim 1 further including a control apparatus mounted near said proximal end of said tubular member, said control apparatus being coupled to the distal end of said tubular member whereby the control apparatus may be selectively operated to transversely flex the tubular member for controllably position the distal end of the tubular member.

3. The device of claim 2 in which said control apparatus includes a control lever disposed at the proximal end of said tubular member and a wire coupling the control lever to said distal end of said tubular member.

4. The device of claim 1 further including a cup mounted on said distal end of said tubular body, said marking device being mounted on the distal end, said needle and said marking device being maintainable in a retracted position in said cup during positioning of said needle relative to the bodily tissue, said needle and said marking device being subsequently extendable from said cup when said needle is intended to penetrate the bodily tissue.

5. The device of claim 4 further including a syringe for containing the therapeutic substance, and a flexible tube, said syringe being in fluid communication with said needle through said flexible tube, said syringe being movable relative to said tubular member for extending said needle and said marking device.

6. The device of claim 1 further including an electrode located at said distal end for providing an electrical indication when said needle has penetrated the targeted bodily tissue.

7. The device of claim 1 wherein the marking device comprises a virtual marking system including a computer and a coupling to the distal end whereby movements of the needle are virtually marked.

8. The device of claim 1 wherein the marking device comprises a radiographic contrasting agent such that the discernible indication may be radiographically detected.

9. The device of claim 1 wherein the marking device comprises an ultrasonically dense marker such that the discernible indication may be ultrasonically detected.

10. The device of claim 1 wherein the marking device includes an electrode at least a portion of which is disposed substantially adjacent the distal end which provides an indication of when the needle enters said bodily tissue, and a coupling to an electrocardiographic display device such that the discernible indication may be electrocardiographically viewed.

11. The device of claim 1 wherein the marking device includes an agent, dye, or other viewable dense substance injected with the therapeutic substance.

12. The device of claim 1 wherein the marking device includes an agent, dye or other viewable dense substance which provides the discernible indication.

13. A method of delivering sequential injections of a therapeutic substance to an area of bodily tissue within the body of a patient, said method comprising:
   providing an elongate tubular body having a proximal end and a distal end, said tubular body having a needle disposed at said distal end;
   inserting the distal end of said tubular body into the patient's body;
   positioning said distal end and said needle proximate to the bodily tissue to be treated;
   penetrating said bodily tissue with said needle;
   injecting said therapeutic substance;
   marking said tissue using a marking device to provide a discernible indication of the location of the injection;
   viewing the discernible indication; and
   repositioning said distal end proximate to the bodily tissue in a location different from the first injection site for making a subsequent injection.

14. The method of claim 13 further including the step of delivering sequential injections in a grid pattern.

15. The method of claim 13 wherein the injecting step includes the step of injecting an angiogenesis-promoting substance.

16. The method of claim 13 wherein said inserting step comprises the steps of making an incision in the patient's body and inserting the distal end of said tubular body into the patient through the incision in the patient's body.

17. The method of claim 13 wherein the positioning step comprises the step of retaining said needle in a retracted position and said penetrating step comprises the step of extending said needle to penetrate the tissue.

18. The method of claim 13 in which the therapeutic substance is retained within a syringe in fluid communication with said needle, and further comprises the step of depressing a plunger of said syringe to inject the therapeutic substance.

19. The method of claim 13 wherein a platen having a raised ring is provided at the distal end of the tubular body, said platen and said needle being fixed relative to each other, wherein the penetrating step includes the step of penetrating the tissue with the needle until the raised ring of said platen contacts the tissue surface for controlling the depth of penetration by said needle, and the marking step includes the step of said raised ring marking said tissue.

20. The method of claim 13 wherein the step of marking said tissue comprises the steps of coupling the needle to a computer and recording and virtually marking the movements of the needle and location of the injection in a virtual marking system.

21. The method of claim 13 wherein the step of marking said tissue comprises the step of providing a discernible indication when an electrode disposed substantially adjacent the distal tip contacts said bodily tissue and the viewing step includes the step of viewing the discernible indication electrocardiographically.

22. The method of claim 13 wherein the step of marking said tissue comprises the step of marking said tissue with an agent, dye, or other viewable dense substance to provide the discernible indication.

23. A method of delivering a therapeutic substance to the heart tissue of a patient, said method comprising:
   at least partially collapsing one of the patient's lungs;
   inserting a delivery device into the patient's thoracic cavity through an opening in the patient's chest wall, said delivery device having a needle for injecting the therapeutic substance into the heart tissue; and
   delivering the therapeutic substance to the patient's heart by passing the needle through the patient's pericardium and into the heart tissue.

24. The method of claim 23 further including the step of marking the location of said injection by marking the pericardium with a discernible indication of the location where the therapeutic substance was delivered.

25. The method of claim 23 further including the step of forming percardiotomies in said pericardium following delivery of the therapeutic substance.

26. The method of claim 23 further including the step of introducing gas into the patient's thoracic cavity to facilitate the at least partial collapse of the patient's lung.

27. The method of claim 23 further including the step of indicating when the heart tissue of the patient has been penetrated by providing an electrode which contacts the patient's heart tissue during injection, said electrode being in electrical connection with a device for indicating when the patient's heart tissue has been penetrated.

28. A method of delivering sequential injections of a therapeutic substance to an area of bodily tissue within the body of a patient, said method comprising:
   at least partially collapsing the patient's lung;
   providing an elongate tubular body having a proximal end and a distal end, said tubular body having a needle disposed at said distal end;
   inserting the distal end of said tubular body into the patient's body after at least partially collapsing the patient's lung;
   positioning said distal end and said needle proximate to the bodily tissue to be treated;
   penetrating said bodily tissue with said needle;
   injecting said therapeutic substance;
   marking said tissue to provide a discernible indication of the location of the injection;
   viewing the discernible indication; and
   repositioning said distal end proximate to the bodily tissue in a location different from the first injection site for making a subsequent injection.

29. A method of delivering sequential injections of a therapeutic substance to an area of bodily tissue within the body of a patient, said method comprising:
   providing an elongate tubular body having a proximal end and a distal end, said tubular body having a needle disposed at said distal end;
   inserting the distal end of said tubular body into the patient's body;
   positioning said distal end and said needle proximate to the bodily tissue to be treated;
   penetrating said bodily tissue with said needle;
   injecting said therapeutic substance;

marking said tissue with a radiographic contrasting agent to provide a discernible indication of the location of the injection;

viewing the discernible indication radiographically; and repositioning said distal end proximate to the bodily tissue in a location different from the first injection site for making a subsequent injection.

30. A method of delivering sequential injections of a therapeutic substance to an area of bodily tissue within the body of a patient, said method comprising:

provluding an elongate tubular body having a proximal end and a distal end, said tubular body having a needle disposed at said distal end;

inserting the distal end of said tubular body into the patient's body;

positioning said distal end and said needle proximate to the bodily tissue to be treated;

penetrating said bodily tissue with said needle;

injecting said therapeutic substance;

marking said tissue with an ultrasonically dense marker to provide a discernible indication of the location of the injection;

viewing the discernible indication ultrasonically; and repositioning said distal end proximate to the bodily tissue in a location different from the first injection site for making a subsequent injection.

31. A method of delivering sequential injections of a therapeutic substance to an area of bodily tissue within the body of a patient, said method comprising:

providing an elongate tubular body having a proximal end and a distal end, said tubular body having a needle disposed at said distal end;

inserting the distal end of said tubular body into the patient's body;

positioning said distal end and said needle proximate to the bodily tissue to be treated;

penetrating said bodily tissue with said needle;

injecting said therapeutic substance;

marking said tissue by injecting an agent, dye or other viewably dense substance with the therapeutic substance to provide a discernible indication of the location of the injection using a marking device;

viewing the discernible indication; and repositioning said distal end proximate to the bodily tissue in a location different from the first injection site for making a subsequent injection.

* * * * *